United States Patent
Scott et al.

(10) Patent No.: US 7,056,116 B2
(45) Date of Patent: Jun. 6, 2006

(54) HEAT SINK FOR DENTAL CURING LIGHT COMPRISING A PLURALITY OF DIFFERENT MATERIALS

(75) Inventors: Robert R. Scott, Riverton, UT (US); Dee Jessop, West Jordan, UT (US)

(73) Assignee: Ultradent Products, Inc., South Jordan, UT (US)

( * ) Notice: Subject to any disclaimer, the term of this patent is extended or adjusted under 35 U.S.C. 154(b) by 0 days.

(21) Appl. No.: 10/973,537

(22) Filed: Oct. 26, 2004

(65) Prior Publication Data

US 2006/0088797 A1 Apr. 27, 2006

(51) Int. Cl.
*A61C 1/00* (2006.01)
*A61C 3/00* (2006.01)

(52) U.S. Cl. ........................................................ 433/29
(58) Field of Classification Search ................ 433/29, 433/32, 150; 372/36
See application file for complete search history.

(56) References Cited

U.S. PATENT DOCUMENTS

| | | |
|---|---|---|
| 3,310,358 A | 3/1967 | Marcatili |
| 3,704,928 A | 12/1972 | Coombs et al. |
| 3,930,149 A | 12/1975 | French |
| 4,184,196 A | 1/1980 | Moret |
| 4,221,994 A | 9/1980 | Friedman et al. |
| 4,229,658 A | 10/1980 | Gonser |
| 4,245,890 A | 1/1981 | Hartman et al. |
| 4,266,535 A | 5/1981 | Moret |
| 4,281,366 A | 7/1981 | Wurster et al. |
| 4,309,617 A | 1/1982 | Long |
| 4,348,180 A | 9/1982 | Schuss |
| 4,385,344 A | 5/1983 | Gonser ........................ 362/32 |
| 4,392,827 A | 7/1983 | Martin |
| 4,522,594 A | 6/1985 | Stark et al. |
| 4,611,992 A | 9/1986 | Lokken |
| 4,666,405 A | 5/1987 | Ericson |
| 4,666,406 A | 5/1987 | Kanca, III |
| 4,682,950 A | 7/1987 | Dragan |
| 4,698,730 A | 10/1987 | Sakai et al. |
| 4,733,937 A | 3/1988 | Lia et al. |
| 4,836,782 A | 6/1989 | Gonser |
| 4,935,665 A | 6/1990 | Murata |
| 4,948,215 A | 8/1990 | Friedman |
| 4,963,798 A | 10/1990 | McDermott |
| 5,013,144 A | 5/1991 | Silverglate et al. |
| 5,013,240 A | 5/1991 | Bailey et al. |
| 5,017,140 A | 5/1991 | Ascher |
| 5,043,634 A | 8/1991 | Rothwell, Jr. et al. |
| 5,071,222 A | 12/1991 | Laakmann et al. |
| 5,115,761 A | 5/1992 | Hood |
| 5,123,845 A | 6/1992 | Vassiliadis et al. |
| 5,139,495 A | 8/1992 | Daikuzono |

(Continued)

*Primary Examiner*—Kevin Shaver
*Assistant Examiner*—Patrick J. Kilkenny
(74) *Attorney, Agent, or Firm*—Workman Nydegger

(57) ABSTRACT

A dental curing light comprises an elongate hollow wand housing having a proximal first end, a distal second end, a light source disposed at the distal second end of the wand housing, and a heat sink disposed at least partially within the wand housing. The heat sink is in contact with the light source, and comprises a plurality of layers or regions comprising different materials. A first layer or region comprises a first material having a higher thermal conductivity than that of a second layer or region, while the second layer or region comprises a second material having a specific heat greater than that of the first layer or region.

23 Claims, 5 Drawing Sheets

U.S. PATENT DOCUMENTS

| | | |
|---|---|---|
| 5,161,879 A | 11/1992 | McDermott |
| 5,275,564 A | 1/1994 | Vassiliadis et al. |
| 5,285,318 A | 2/1994 | Gleckman |
| 5,288,231 A | 2/1994 | Kuehn et al. |
| 5,290,169 A | 3/1994 | Friedman et al. |
| 5,312,249 A | 5/1994 | Kennedy |
| 5,348,552 A | 9/1994 | Nakajima et al. |
| 5,371,826 A | 12/1994 | Friedman |
| 5,382,799 A | 1/1995 | May |
| 5,388,988 A | 2/1995 | Goisser et al. |
| 5,397,892 A | 3/1995 | Abdelqader |
| 5,415,543 A | 5/1995 | Rozmajzl, Jr. |
| 5,420,768 A | 5/1995 | Kennedy |
| D361,382 S | 8/1995 | Brunsell et al. |
| 5,448,323 A | 9/1995 | Clark et al. |
| 5,457,611 A | 10/1995 | Verderber |
| 5,485,317 A | 1/1996 | Perissinotto et al. |
| 5,521,392 A | 5/1996 | Kennedy et al. |
| 5,527,261 A | 6/1996 | Monroe et al. |
| 5,616,141 A | 4/1997 | Cipolla |
| 5,634,711 A * | 6/1997 | Kennedy et al. ............ 362/119 |
| 5,660,461 A | 8/1997 | Ignatius et al. |
| 5,669,769 A | 9/1997 | Disel |
| D385,051 S | 10/1997 | Wu |
| D385,630 S | 10/1997 | Lieb et al. |
| 5,698,866 A | 12/1997 | Doiron et al. |
| 5,711,665 A | 1/1998 | Adam et al. |
| 5,733,029 A | 3/1998 | Monroe |
| 5,749,724 A | 5/1998 | Cheng |
| 5,759,032 A | 6/1998 | Bartel |
| 5,762,605 A | 6/1998 | Cane et al. |
| 5,768,458 A | 6/1998 | Ro et al. |
| 5,772,643 A | 6/1998 | Howell et al. |
| 5,782,553 A | 7/1998 | McDermott |
| 5,791,898 A | 8/1998 | Maissami |
| 5,797,740 A | 8/1998 | Lundvik |
| 5,803,729 A | 9/1998 | Tsimerman |
| 5,880,839 A | 3/1999 | Ishizuka et al. |
| 5,885,082 A | 3/1999 | Levy |
| 5,897,314 A | 4/1999 | Hack et al. ............ 433/29 |
| 5,905,268 A | 5/1999 | Garcia et al. |
| 5,908,294 A | 6/1999 | Schick et al. |
| 5,908,295 A | 6/1999 | Kawata |
| 5,912,470 A | 6/1999 | Eibofner et al. |
| 5,921,777 A | 7/1999 | Dorman |
| 5,971,755 A | 10/1999 | Liebermann et al. |
| 5,975,895 A | 11/1999 | Sullivan |
| 6,001,058 A | 12/1999 | Sano et al. |
| 6,008,264 A | 12/1999 | Ostler et al. |
| 6,019,482 A | 2/2000 | Everett |
| 6,019,599 A | 2/2000 | Völcker et al. |
| 6,028,694 A | 2/2000 | Schmidt |
| 6,033,087 A | 3/2000 | Shozo et al. |
| 6,033,223 A | 3/2000 | Narusawa et al. |
| 6,036,336 A | 3/2000 | Wu |
| 6,059,421 A | 5/2000 | White et al. |
| 6,068,474 A | 5/2000 | Senn et al. |
| 6,077,073 A | 6/2000 | Jacob |
| 6,086,366 A | 7/2000 | Mueller et al. |
| 6,089,740 A | 7/2000 | Forehand et al. |
| 6,095,661 A | 8/2000 | Lebens et al. |
| 6,095,812 A | 8/2000 | Senn et al. |
| 6,099,520 A | 8/2000 | Shimoji |
| 6,102,696 A | 8/2000 | Osterwalder et al. |
| 6,103,203 A | 8/2000 | Fischer |
| 6,123,545 A | 9/2000 | Eggler et al. |
| 6,155,823 A | 12/2000 | Nagel |
| 6,159,005 A | 12/2000 | Herold et al. |
| 6,200,134 B1 | 3/2001 | Kovac et al. |
| 6,208,788 B1 | 3/2001 | Nosov |
| 6,210,427 B1 * | 4/2001 | Augustine et al. ............ 607/96 |
| 6,224,623 B1 * | 5/2001 | Augustine et al. ............ 607/104 |
| 6,270,343 B1 | 8/2001 | Martin |
| 6,280,187 B1 | 8/2001 | Stone |
| 6,282,013 B1 | 8/2001 | Ostler et al. |
| 6,307,871 B1 * | 10/2001 | Heberle ............ 372/34 |
| 6,318,996 B1 | 11/2001 | Melikechi et al. |
| 6,322,358 B1 | 11/2001 | Senn et al. |
| 6,325,623 B1 | 12/2001 | Melnyk et al. |
| 6,328,456 B1 | 12/2001 | Mize |
| 6,331,111 B1 * | 12/2001 | Cao ............ 433/29 |
| 6,361,192 B1 | 3/2002 | Fussell et al. |
| 6,361,489 B1 | 3/2002 | Tsai |
| 6,398,398 B1 | 6/2002 | Moschkowitz |
| 6,402,511 B1 | 6/2002 | Calderwood |
| 6,417,917 B1 | 7/2002 | Jung et al. |
| 6,419,483 B1 * | 7/2002 | Adam et al. ............ 433/29 |
| 6,439,888 B1 * | 8/2002 | Boutoussov et al. ............ 433/215 |
| 6,465,961 B1 | 10/2002 | Cao |
| 6,468,077 B1 | 10/2002 | Melikechi et al. |
| 6,478,447 B1 | 11/2002 | Yen |
| 6,480,515 B1 * | 11/2002 | Wilson ............ 372/36 |
| 6,482,004 B1 | 11/2002 | Senn et al. |
| 6,485,301 B1 | 11/2002 | Gemunder et al. |
| 6,511,317 B1 | 1/2003 | Melikechi et al. |
| 6,511,321 B1 | 1/2003 | Trushkowsky et al. |
| 6,514,075 B1 | 2/2003 | Jacob |
| 6,611,110 B1 * | 8/2003 | Fregoso ............ 315/224 |
| 6,622,786 B1 * | 9/2003 | Calmidi et al. ............ 165/185 |
| 6,666,875 B1 | 12/2003 | Sakurai et al. ............ 606/169 |
| 6,692,251 B1 | 2/2004 | Logan et al. |
| 6,692,252 B1 * | 2/2004 | Scott ............ 433/29 |
| 6,709,128 B1 | 3/2004 | Gordon et al. |
| 6,719,558 B1 | 4/2004 | Cao |
| 6,719,559 B1 | 4/2004 | Cao |
| 6,755,648 B1 | 6/2004 | Cao |
| 6,783,362 B1 * | 8/2004 | Cao ............ 433/29 |
| 2001/0038992 A1 | 11/2001 | Otsuka |
| 2001/0046652 A1 | 11/2001 | Ostler et al. |
| 2001/0055451 A1 | 12/2001 | Kuhara et al. |
| 2002/0073921 A1 | 6/2002 | Russell et al. |
| 2002/0085372 A1 | 7/2002 | Lehrer |
| 2002/0093833 A1 | 7/2002 | West |
| 2002/0102513 A1 | 8/2002 | Plank |
| 2002/0115037 A1 | 8/2002 | Cao |
| 2002/0133970 A1 | 9/2002 | Gordon et al. |
| 2002/0147383 A1 | 10/2002 | Weber et al. |
| 2002/0163317 A1 | 11/2002 | Cao |
| 2002/0167283 A1 | 11/2002 | Cao |
| 2002/0168306 A1 | 11/2002 | Cao |
| 2002/0168604 A1 | 11/2002 | Cao |
| 2002/0168605 A1 | 11/2002 | Cao |
| 2002/0168606 A1 | 11/2002 | Cao |
| 2002/0168607 A1 | 11/2002 | Cao |
| 2002/0168608 A1 | 11/2002 | Cao |
| 2002/0172912 A1 | 11/2002 | Cao |
| 2002/0172913 A1 | 11/2002 | Cao |
| 2002/0172914 A1 | 11/2002 | Cao |
| 2002/0172915 A1 | 11/2002 | Cao |
| 2002/0172916 A1 | 11/2002 | Cao |
| 2002/0172917 A1 | 11/2002 | Cao |
| 2002/0175352 A1 | 11/2002 | Cao |
| 2002/0175628 A1 | 11/2002 | Cao |
| 2002/0177095 A1 | 11/2002 | Cao |
| 2002/0177096 A1 | 11/2002 | Cao |
| 2002/0177099 A1 | 11/2002 | Cao |
| 2002/0180368 A1 | 12/2002 | Cao |
| 2002/0181947 A1 | 12/2002 | Cao |
| 2002/0182561 A1 | 12/2002 | Cao |
| 2002/0182562 A1 | 12/2002 | Cao |
| 2002/0187454 A1 | 12/2002 | Melikechi et al. |
| 2002/0187455 A1 | 12/2002 | Melikechi et al. |
| 2002/0190659 A1 | 12/2002 | Cao |
| 2002/0190660 A1 | 12/2002 | Cao |

| | | |
|---|---|---|
| 2002/0197582 A1 | 12/2002 | Cao |
| 2003/0001507 A1 | 1/2003 | Cao |
| 2003/0036031 A1 | 2/2003 | Lieb et al. |
| 2003/0038291 A1 | 2/2003 | Cao |
| 2003/0039119 A1 | 2/2003 | Cao |
| 2003/0039120 A1 | 2/2003 | Cao |
| 2003/0039122 A1 | 2/2003 | Cao |
| 2003/0040200 A1 | 2/2003 | Cao |
| 2003/0081430 A1 | 5/2003 | Becker |
| 2003/0133203 A1 | 7/2003 | McLean et al. |
| 2003/0133298 A1 | 7/2003 | Cao |
| 2003/0142413 A1 | 7/2003 | McLean et al. |
| 2003/0147254 A1 | 8/2003 | Yoneda et al. |
| 2003/0147258 A1 | 8/2003 | Fischer et al. |
| 2003/0148242 A1 | 8/2003 | Fischer et al. |
| 2003/0152885 A1 | 8/2003 | Dinh |
| 2003/0186195 A1 | 10/2003 | Comfort et al. |
| 2003/0215766 A1 | 11/2003 | Fischer et al. |
| 2003/0218880 A1 | 11/2003 | Brukilacchio |
| 2003/0219693 A1 | 11/2003 | Cao |
| 2003/0219694 A1 | 11/2003 | Bianchetti et al. |
| 2003/0235800 A1 | 12/2003 | Qadar |
| 2004/0018762 A1* | 1/2004 | Takayama et al. .......... 439/266 |
| 2004/0033033 A1 | 2/2004 | Hoshino et al. |

* cited by examiner

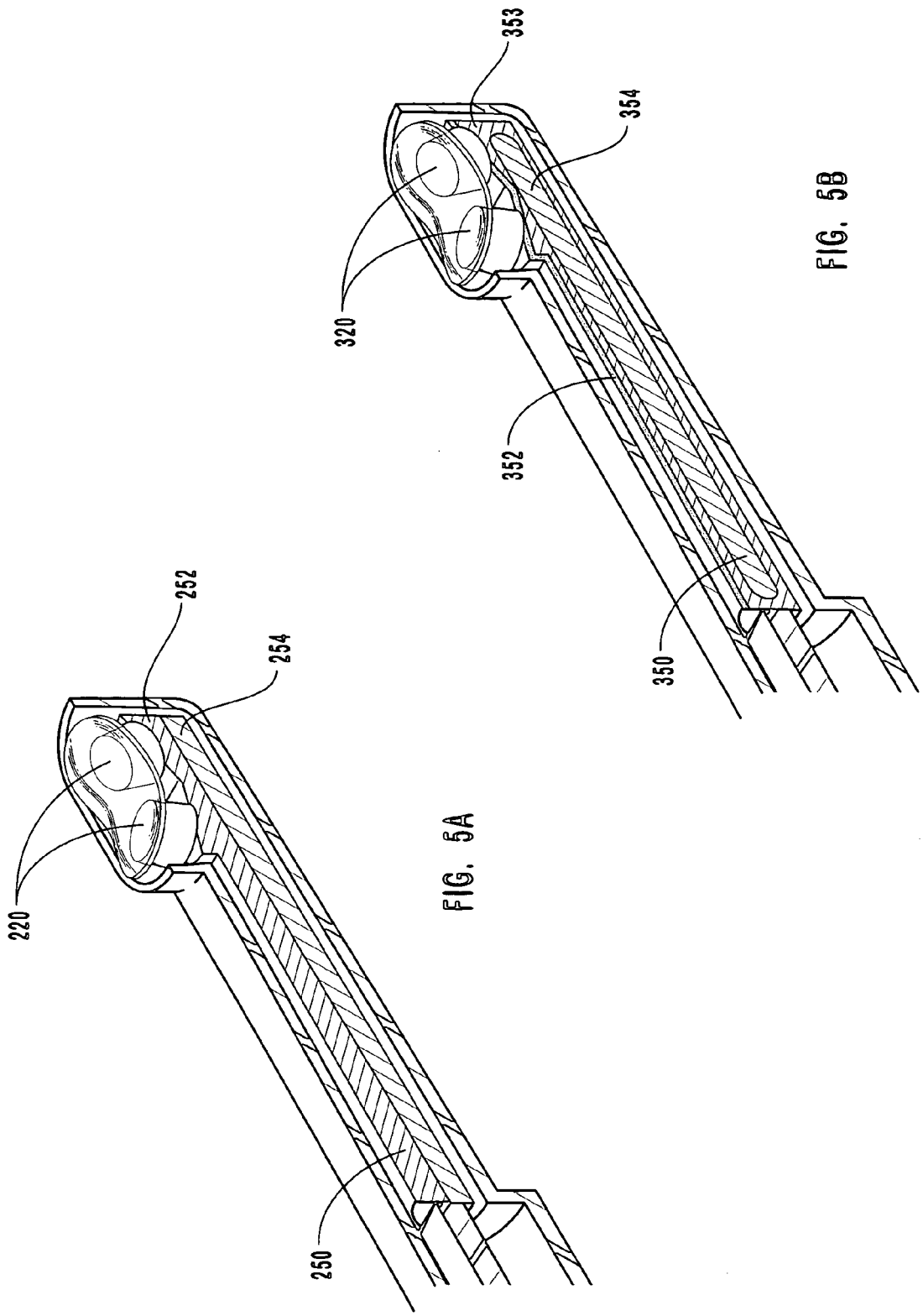

HEAT SINK FOR DENTAL CURING LIGHT COMPRISING A PLURALITY OF DIFFERENT MATERIALS

BACKGROUND OF THE INVENTION

1. The Field of the Invention

The present invention generally relates to the field of light curing devices incorporating light sources and, more particularly, to the field of heat sinks configured for dissipating heat generated by the light sources of the light curing devices.

2. The Relevant Technology

In the field of dentistry, dental cavities are often filled and/or sealed with photosensitive compounds that are cured when they are exposed to radiant energy, such as visible or ultraviolet light. These compounds, commonly referred to as light-curable compounds, are placed within dental cavity preparations or onto dental surfaces where they are subsequently irradiated by a light-curing dental device.

Many light-curing devices are configured with a fiber optic wand for directing light from a light source into a patient's mouth. The light source may comprise, for example, a lamp, a halogen bulb or a light-emitting diode (LED). One end of the fiber optic wand is placed close to the light source so that the light emitted from the light source will be directed into the fiber optic wand. One problem with fiber optic wands is that they are generally unable to capture all of the light that is generated by the light source, particularly light emitted by LEDs, which may be emitted at angles of up to about 120°. Another problem is that fiber optic wands, being essentially solid glass, are relatively heavy and bulky.

One method for overcoming the limitations of fiber optic wands and for generally improving the lightness and efficiency of the light-curing devices is to place the light source(s) of the light-curing device at the end of the light-curing device that is placed next to the composition being cured. Although this addressed problems associated with fiber optic wands, the proximity of the light source(s) to the patient's mouth creates its own problems. For example, heat generated by the light source(s) at the tip of the light-curing device can cause patient discomfort when the tip of the light-curing device happens to come in contact or immediate proximity to the sensitive mouth tissues of the patient. Accordingly, it is desirable to minimize the heat at the tip of the light-curing device.

One method for minimizing the heat at the tip of the light-curing device is to mount the light source(s) on a heat sink that can conduct heat away from the tip of the light-curing device. The ability of a heat sink to absorb and dissipate heat is generally controlled by the material properties and geometries of the heat sink. The arrangement and geometries of the mounting surfaces of the heat sink are also important factors to consider when determining how efficiently the heat sink will be able to absorb and dissipate heat.

Typically, heat sinks are formed of a homogenous material, for example a metal or metal alloy. The material properties that most affect the ability of a given material to act as an effective heat sink are thermal conductivity and specific heat of the material. Heat sink materials may be selected so as to have a high thermal conductivity or a high specific heat. When selecting a material for its high thermal conductivity, the material's specific heat may be lower than desired. Also, when selecting a material for its high specific heat, the material's thermal conductivity may be lower than desired.

It would be an improvement in the art to provide a heat sink formed of a plurality of layers or regions of different materials so as to increase the ability to absorb and dissipate heat.

BRIEF SUMMARY OF THE PREFFERED EMBODIMENTS

The present invention is directed to a dental curing light having a heat sink specifically configured for effectively dissipating and absorbing heat generated by one or more light sources (e.g., LEDs) away from the tip of the dental curing light.

According to one embodiment, the dental curing light comprises an elongate hollow wand housing having a proximal first end, a distal second end, a light source disposed at the distal second end of the wand housing, and a heat sink disposed at least partially within the wand housing. The heat sink is in contact with the light source, and comprises a plurality of layers or regions comprising different materials. A first layer or region comprises a first heat sink material, while a second layer or region comprises a second heat sink material different from the first material. The thermal conductivity of the first heat sink material is greater than that of the second heat sink material, and the specific heat of the second heat sink material is greater than the specific heat of the first material.

Thermal conductivity generally quantifies the ability of a given material to conduct and dissipate heat to the surrounding environment. Specific heat generally quantifies the ability of a given material to absorb heat.

According to one embodiment, the first material (i.e., having a higher thermal conductivity) may comprise at least one of copper, aluminum, brass, steel, silver, another metal, a metal oxide ceramic, diamond, graphite, carbon fiber, or even a polymer based epoxy, silicone, or any other material having a higher thermal conductivity than the selected second material.

According to one embodiment, the second material (i.e., having a higher specific heat) may comprise at least one of water, copper (so long as copper is not also used as the first material), nickel, beryllium, or any other material having a higher specific heat than the selected first material. According to some embodiments, the second layer or region may comprise a solid, a liquid, or a gas core within the heat sink. It may comprise a solid or liquid material that undergoes a phase change above room temperature (e.g., up to 135° C.) in order to absorb additional heat without causing a proportionate increase in temperature (e.g., waxes, water, salt, fatty acids and esters, polyols, other hydrocarbons, iodine, and gallium).

Because specific heat is measured on a per unit mass basis, and because the volume of the heat sink may be relatively small, it may be advantageous in some embodiments for the second material to also have a relatively high density. The product of the selected material's density and specific heat quantifies the amount of heat that the second layer or region can absorb. According to one such embodiment, the product of the density of the second material and its second specific heat is greater than the product of the density of the first material and its specific heat.

Each layer or region within the inventive heat sink is optimized for a particular purpose. The first layer or region acts to draw and conduct heat away from the one or more light sources. The second layer or region acts as a "sink" which absorbs heat already conducted away from the light source. The first layer or region may also act to dissipate heat into the air, away from the one or more light sources. The overall effect is a heat sink which effectively draws heat away from the one or more light sources, provides for its absorption, and allows cooler operation of the light source(s) (e.g., LEDs) and the dental curing light.

According to one embodiment, at least a portion of the heat sink may be separated from the wand housing by an air gap. The air gap provides insulation, resulting in less heat diffusing out of the housing wand of the dental curing light in the region around the tip of the curing light, resulting in a cooler tip and greater comfort for the patient.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 5A is a cross sectional view of an alternative heat sink suitable for use with a dental curing light; and FIG. 5B is a cross sectional view of another alternative heat sink suitable for use with a dental curing light.

DETAILED DESCRIPTION OF THE PREFERRED EMBODIMENTS

I. Definitions and Introduction

A detailed description of the curing light of the invention will now be provided with specific reference to figures illustrating preferred embodiments of the invention. It will be appreciated that like structures will be provided with like reference designations.

The term "specific heat" is a parameter characterizing the quantity of heat required to produce a unit temperature rise per unit mass of material. The units of measure for specific heat are J/kg-K.

The term "thermal conductivity" is a parameter characterizing the ability of a material to conduct heat. The units of measure for thermal conductivity are J/sec-m-K.

The term "light source" includes any light source known in the art suitable for use with dental curing lights, examples of which include incandescent lamps, halogen bulbs, light-emitting diodes (LEDs), and LED arrays. The term "LED light source" includes the electrical components of the LED as well as the integral lens or micro lens of the typical LED structure.

In general, the dental curing light comprises an elongate hollow wand housing having a proximal first end, a distal second end, at least one light source disposed at the distal second end of the wand housing, and a heat sink in contact with the light source and disposed within the wand housing.

The heat sink comprises a plurality of layers or regions comprising different materials. According to one embodiment, a first layer or region comprises a first material having a first thermal conductivity and a first specific heat, while a second layer or region comprises a second material having a second thermal conductivity and a second specific heat. The thermal conductivity of the first material is greater than the thermal conductivity of the second material, while the specific heat of the second material is greater than that of the first material.

II. Exemplary Dental Curing Light

Figure 1:
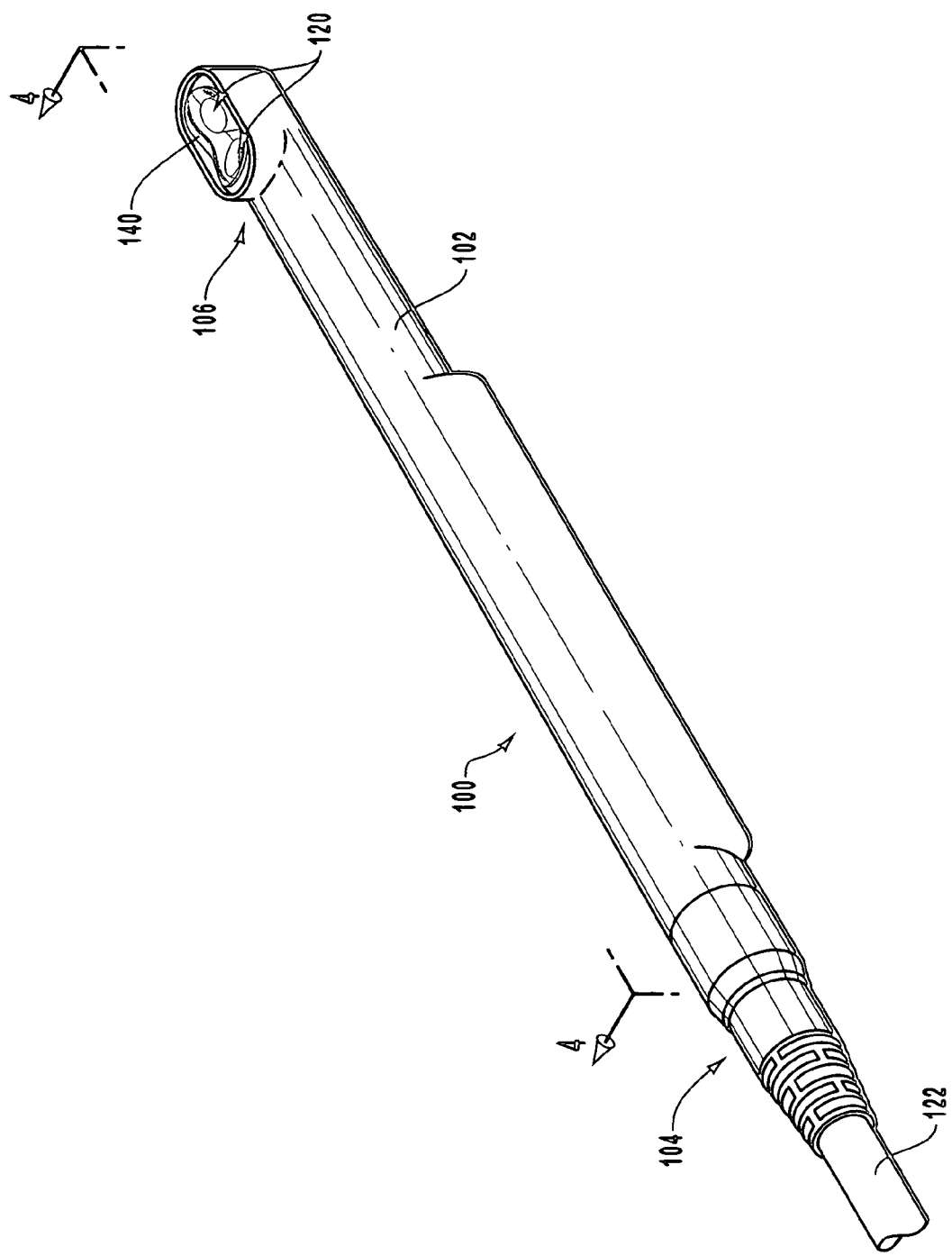
FIG. 1 is a bottom perspective view of a dental curing light according to the invention.

Reference is first made to FIG. 1, which is a bottom perspective view of one embodiment of a dental curing light 100. As shown, the dental curing light 100 includes an elongate housing 102 that extends between a proximal first end 104 and a distal second end 106. Although the housing 102 is shown to be sleek and slender, it will be appreciated that the housing 102 of the dental curing light 100 may comprise any desired shape and size.

A light source 120 disposed at the distal end 106 of the dental curing light 100 is configured to emit light suitable for curing light-curable compounds, such as, for example, during dental restoration procedures. The light source 120, as shown, includes two LEDs. Although only two LEDs are shown, it will be appreciated that the light source 120 may also include more or less than two LEDs or other light sources. The light source 120 may also include an LED array, a plurality of LED arrays, and any combination of LEDs and LED arrays. The curing light 100 may also include a lens 140 sized and configured so as to cover the light source 120 at the distal end 106 of the body 102 and to focus light emitted by the light source 120.

According to one embodiment of the invention, the light source 120 and the distal end 106 of the elongate housing 102 are sized and configured so as to be easily inserted into the mouth of a patient, thereby enabling light generated by the light source 120 to be directly emitted into the patient's mouth without first passing through an elongated light guide (e.g., a fiber optic wand), as required by many conventional light curing devices.

According to one embodiment, the light source 120 is powered by a remote electrical power supply (not shown), which may include, but is not limited to, the power outlet of a wall receptacle, a battery, a generator, a transformer or any other source capable of supplying power to the dental curing light. A power cord 122 connected at the proximal end 104 of the dental curing light 100 operably connects the remote power supply with the dental curing light 100.

According to one alternative embodiment (not shown), the proximal end 104 of the dental curing light is not connected to a power cord 122, but rather the dental curing light 100 is equipped with an integral battery pack that is capable of powering the dental curing light 100 and energizing the light source. The battery pack is advantageously rechargeable (e.g., by direct electrical contact or by induction).

Figure 2:
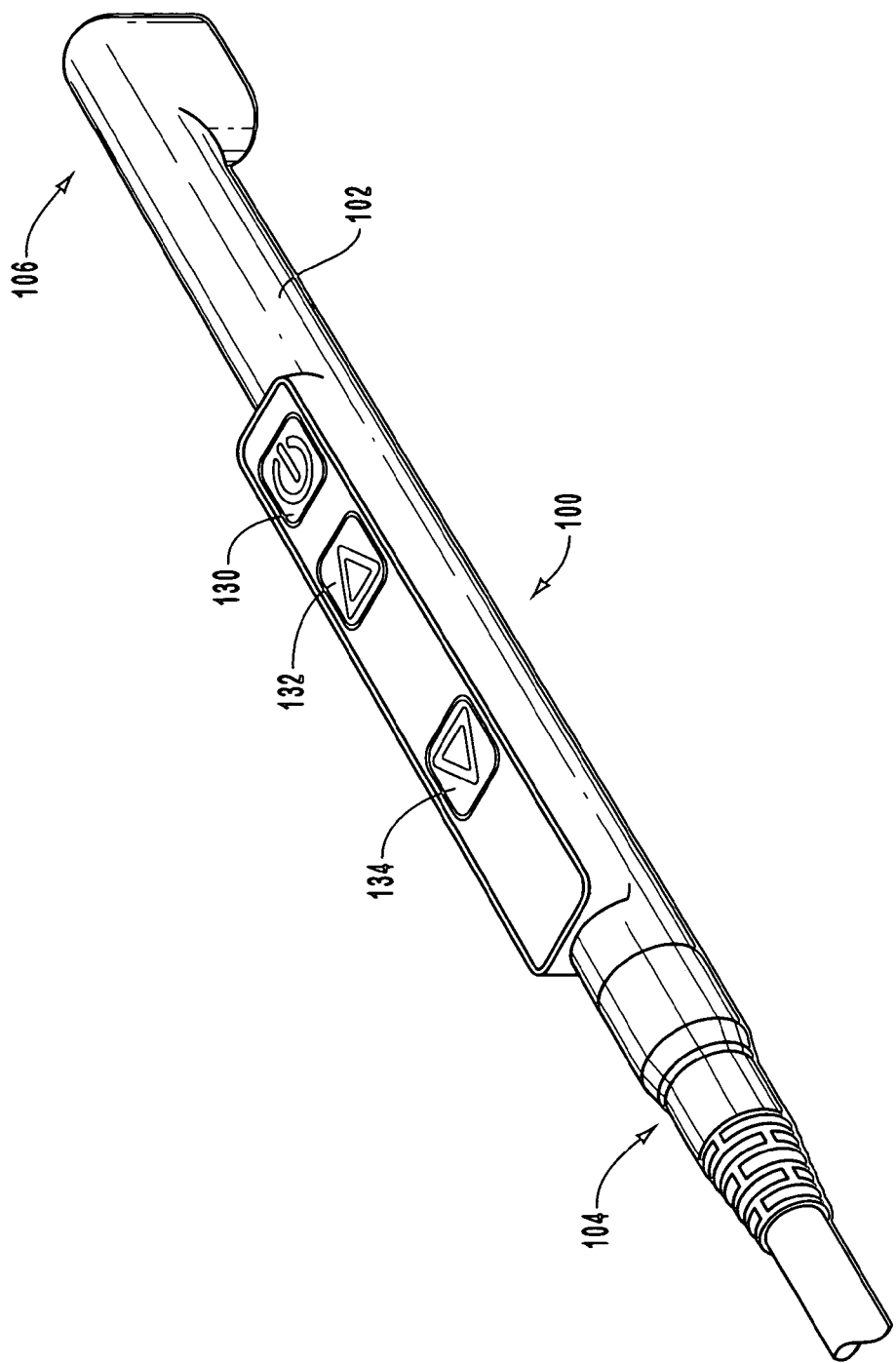
FIG. 2 is an top perspective view of the curing light of FIG. 1.

FIG. 2 is a top perspective view of the dental curing light 100 shown in FIG. 1 and further illustrates controls that are disposed on the elongate housing 102 of the dental curing light 100. According to this embodiment, the controls are configured to enable a dental practitioner to control the activation of the light source 120.

According to this embodiment, the controls preferably include three different buttons 130, 132, 134. The first button 130, when depressed, selectively activates and deactivates the light source 120. In one embodiment, first button 130, when depressed, may activate the light source for a predetermined duration of time, such as, for example, 15 seconds, thereby enabling the dental practitioner to use the dental curing light 100 without having to continuously depress button 130 during use. The second and third buttons 132, 134 can be designed to increase or decrease the predetermined duration of time light is emitted by a desired increment of time, such as, for example, by 5 second increments. Alternatively, second and third buttons 132, 134 can be designed to selectively increase or decrease the intensity of light that is emitted. The buttons could alternatively be designed to switch between ramped, pulsed or continuous light output. Various embodiments of dental curing lights with ramped and pulsed output are disclosed in U.S. patent application Ser. No. 10/916,283, filed Aug. 11, 2004, and titled CURING LIGHT WITH RAMPED OR PULSED LEDS, which is hereby incorporated by reference with respect to its disclosure of curing lights having ramped or pulsed LEDs. The curing light 100 may, of course, include any desired number and functionality of buttons or controls.

The controls are advantageously ergonomically mounted on the elongate housing 102 of the dental curing light 100 for ease of use. In particular, the controls are advantageously disposed on the body 102 in a manner which enables them to be manipulated by the thumb or finger of the dental practitioner. It will be appreciated, however, that the dental curing light 100 of the invention is not limited to any particular configuration or type of controls. Rather, the dental curing lights of the invention may be configured with any type of controls that are attached to the body of the dental curing light or that are remotely located away from the curing light, as desired.

Figure 3:
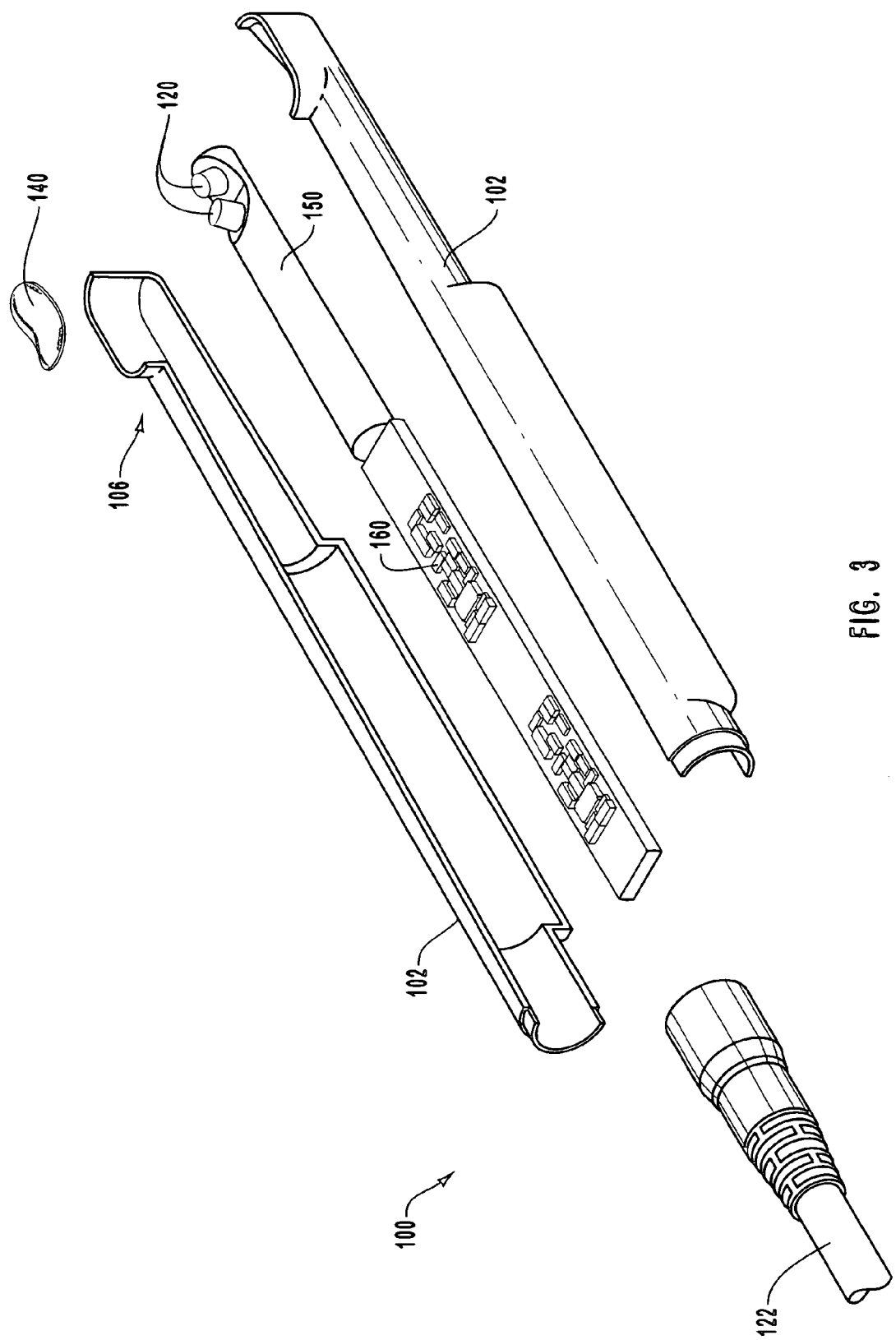
FIG. 3 is an exploded view of the dental curing light of FIGS. 1 and 2.

Referring to FIG. 3, the dental curing light 100 also includes electronic circuitry 160 for controlling the operation of the curing light through buttons 130, 132, and 134 (or alternative controls) as illustrated and described in conjunction with FIG. 2. Power may be provided to the electronic circuitry 160 through an electrical connection (not shown) to power cord 122. Additional wiring (not shown) to provide power and control between the electronic circuitry 160 and the LEDs 120 may also be included, as desired.

Figure 4:
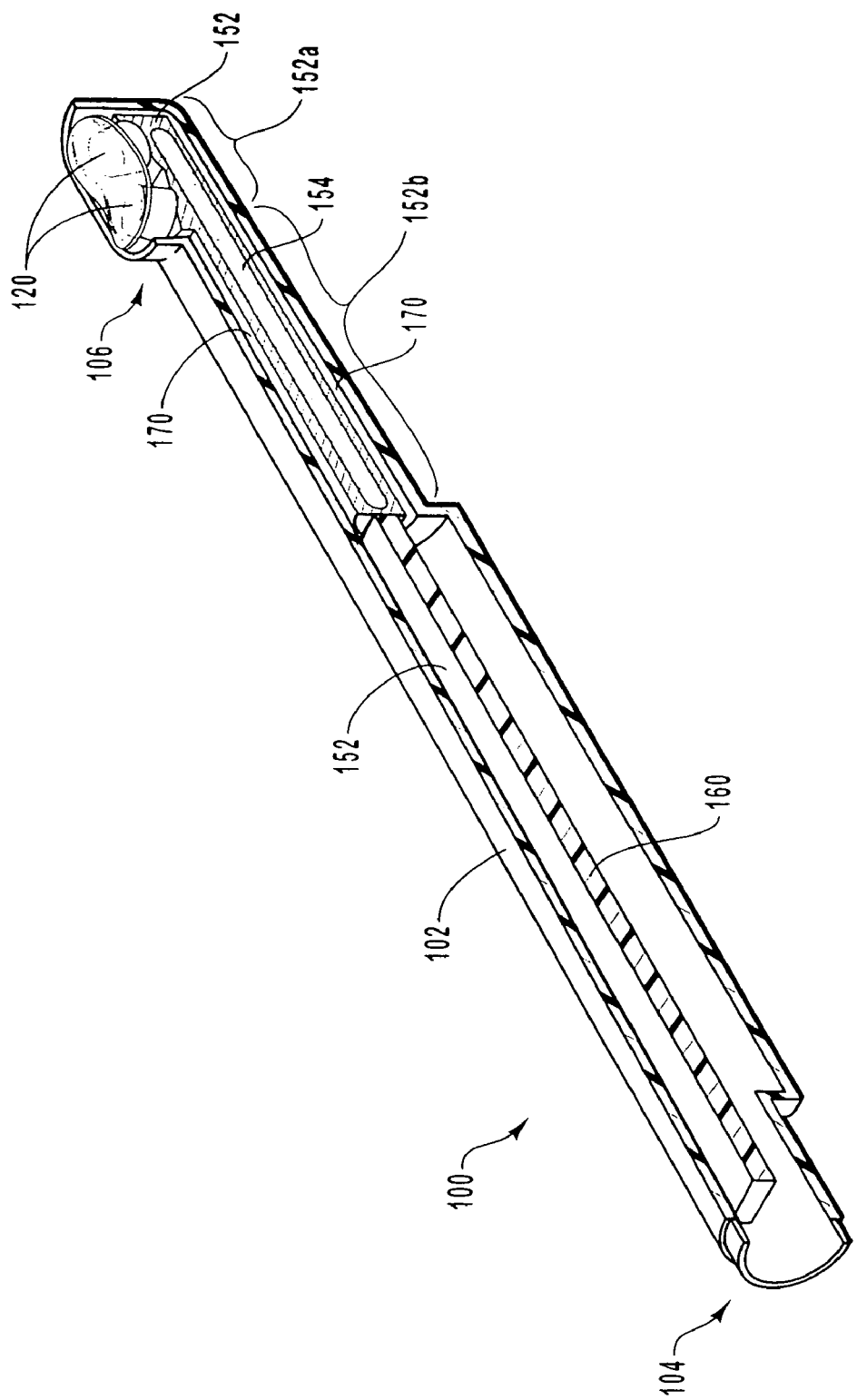
FIG. 4 is a cross sectional view of the dental curing light of FIGS. 1 and 2 taken along cutting line 4—4.

FIGS. 3 and 4 illustrate an exploded view and a cross sectional view, respectively, of the dental curing light 100. As can be seen in FIG. 3, the elongate housing 102 is hollow so as to allow room for the internal components of the dental curing light 100. The light source (e.g., LEDs) 120 may be mounted to heat sink 150. In any case, the heat sink 150 is configured so as to be adjacent to the light source 120 so as to draw away excess heat produced by the light source 120.

The heat sink 150 is formed of a plurality of layers or regions. FIG. 4 illustrates one embodiment of a heat sink 150 having two layers or regions. First layer or region 152 is formed of a first material having a first thermal conductivity and a first specific heat. Second layer or region 154 is formed of a second material having a second thermal conductivity and a second specific heat. The thermal conductivity of the first material is greater than the thermal conductivity of the second material, while the specific heat of the second material is greater than the specific heat of the first material.

In the illustrated embodiment, layer or region 154 also comprises a core within heat sink 150. Such a core may comprise a solid, a liquid, or a gas. In this way, the portion 152a of the first region 152 adjacent to the light source 120 helps draw heat away from the light source 120 and conduct or "deposit" it to the second region 154, and the portion 152b of the first region separated from the light source by the second region 154 helps draw and dissipate heat away from the second region 154.

According to one embodiment, first layer or region 152 may comprise at least one of copper, aluminum, brass, steel, silver, another metal, a metal oxide ceramic, diamond, graphite, carbon fiber, silicon carbide, or even a polymer based epoxy or silicone. The thermal conductivity of the material within the first region is preferably at least about 120 J/sec-m-k, more preferably at least about 240 J/sec-m-k, and most preferably at least about 350 J/sec-m-k.

According to one embodiment, second layer or region 154 may comprise at least one of water, copper, nickel, beryllium, aluminum, magnesium, silicon, or any other material having a specific heat greater than the specific heat of the selected first material. The second layer or region may comprise a solid, liquid or gas core encapsulated within the first layer or region. It may comprise a solid or liquid material that undergoes a phase change in order to absorb additional heat without causing a proportionate increase in temperature. In other words, heat is absorbed when the substance undergoes a phase change (e.g., solid to liquid, solid to gas, or liquid to gas) without a concomitant rise in temperature. In the context of a dental curing light, the phase change would advantageously occur between room temperature and about 135° C. Examples of materials that undergo a phase change include, but are not limited to, waxes (e.g., paraffin), water, Glauber's salt (sodium sulfate decahydrate), calcium chloride hexahydrate, linear crystalline alkyl hydrocarbonds, fatty acids, fatty esters, polyethylene glycols, long alkyl side chain polymers, pentaerythritol, pentaglycerine, neopentyl glycol, low melting metals and alloys, quaternary ammonium clathrates and semi-clathrates, salt hydrides, iodine, and gallium.

The specific heat of the material within the second region is preferably at least about 380 J/Kg-k, more preferably at least about 900 J/Kg-k, and most preferably at least about 1800 J/Kg-k. The product of the specific heat and density of the material (i.e., "heat density") in the second region is preferably at least about 3 $J/cm^3$-k, more preferably at least about 3.3 $J/cm^3$-k, and most preferably at least about 3.5 $J/cm^3$-k.

Because specific heat is measured on a per unit mass basis, and because the volume of the heat sink may be relatively small and fixed, it may be advantageous in some embodiments for the second material to also have a relatively high density. The product of the selected material's density and specific heat quantifies the amount of heat that the second layer or region can absorb. According to one such embodiment, the product of the density of the second material and the second specific heat is greater than the product of the density of the first material and the first specific heat.

Table I below provides the densities, specific heats, thermal conductivities, and the heat densities (i.e., the products of density and specific heat) for some exemplary materials.

TABLE I

Properties of Various Materials

| MATER-IAL | DENSITY g/cm³ | SPECIFIC HEAT J/kg-K | Product of Density and Specific Heat J/cm³-K | THERMAL CONDUCTIVITY J/sec-m-K |
|---|---|---|---|---|
| Water | 1 | 4186 | 4.19 | 0.66 |
| Copper | 8.945 | 384 | 3.43 | 398 |
| Nickel | 8.9 | 445 | 3.96 | 91 |
| Beryllium | 1.85 | 1820 | 3.37 | 218 |
| Aluminum | 2.71 | 905 | 2.45 | 237 |
| Brass | 8.4 | 385 | 3.23 | 109 |
| Steel (316SS) | 8 | 460 | 3.68 | 13.5 |
| Silver | 10.52 | 236 | 2.48 | 427 |
| Diamond | 3.52 | 610 | 2.15 | ~2000 |
| Graphite[1] | ~2.25 | ~720 | ~1.4 | ~80–2000 |
| Carbon Fiber[2] | ~2 | ~700 | ~1.4 | ~350–900 |
| $CO_2$ (gas)[3] | 0.0018 | ~837 | 1.5 | 0.015 |
| Magnesium | 1.746 | 1023 | 1.79 | 156 |
| Silicon | 2.33 | 700 | 1.63 | 149 |
| Silicon Carbide[4] | 3.1 | 640–750 | 1.98–2.32 | 100–350 |

[1]Varies based on structure
[2]Varies based on method of manufacture
[3]Varies based on temperature and pressure
[4]Varies based on structure The inclusion of a plurality of layers or regions, with each layer or region selected so as to have desired properties with respect to thermal conductivity and specific heat allows the heat sink to more effectively draw away, dissipate, and absorb excess heat. First layer or region 152 acts to quickly and effectively draw excess heat away from LED light source 120. Second layer or region 154 acts to efficiently absorb and maintain the excess heat away from the LED. In addition, because second layer or region 154 comprises a core, the first layer or region 152 may also act to further dissipate excess heat into the air so as to further cool the LED light source 120.

FIG. 5A illustrates an alternative embodiment of a heat sink 250 that includes a first layer or region 252 and a second layer or region 254. According to one such embodiment, first layer or region 252 is formed of a first material (e.g., copper or aluminum) having a first thermal conductivity greater than the thermal conductivity of the second material of second layer or region 254, while second layer or region 254 is formed of a second material having a second specific heat greater than the specific heat of the first material.

FIG. 5B illustrates another alternative embodiment of a heat sink 350 that includes a first layer or region 352 formed of a first material (e.g., diamond, graphite, or carbon fiber) having a first thermal conductivity and a first specific heat, a second layer or region 353 formed of a second material (e.g., copper) having a second thermal conductivity and a second specific heat, and a third layer or region comprising a core 354 formed of a third material (e.g., water) having a third thermal conductivity and a third specific heat.

According to one such embodiment, the thermal conductivity of the first material is greater than the thermal conductivity of the second material, the thermal conductivity of the second material is greater than the thermal conductivity of the third material, and the specific heat of the third material is greater than the specific heat of the first material.

The first layer or region 352 is located adjacent to the light source 320, and may be relatively thin. The first layer or region 352 comprising a first material may have a thermal conductivity that is very high. For example, the thermal conductivity of the first material may be greater than the thermal conductivity of both the second and third materials. Such an embodiment may draw heat away from light source 320 very quickly. Second layer or region 353 is formed of a second material having a thermal conductivity higher than the thermal conductivity of the third material, which effectively draws heat away from first layer or region 352. The core 354 is formed of a third material having a specific heat higher than the specific heat of the first material. As such, core 354 is able to absorb heat that has been drawn away from light source 320 by first and second layers or regions 352 and 353, respectively.

The relative thickness of each layer or region can be selected as desired. For example, according to one embodiment, the third layer or region comprising a third material having a relatively high specific heat (as compared to the other layers or regions) may comprise a relatively thick core, while the first and second layers or regions comprising materials with relatively high thermal conductivities (as compared to the other layers or regions) may be relatively thin.

According to one embodiment, the heat sink may have a diameter of about ⅜". By way of example, according to one embodiment such as that illustrated in FIG. 5B, first layer 352 may be formed of diamond and have a thickness of about 0.1 inch or less, core 354 may occupy about half of the volume of heat sink 350, with second layer or region 353 occupying the remaining volume.

As illustrated in the cross sectional view of FIG. 4, there may be an insulating layer 170 between the heat sink 150 and the elongate housing 102. According to one embodiment, the insulating layer 170 may be an air gap, although it could alternatively be filled with any known heat-insulating material (e.g., insulating ceramics or polymers). Providing an insulating layer 170 surrounding the heat sink 150 reduces the amount of heat that would otherwise be dissipated out of the distal end of the curing light 100. Reducing dissipation of heat at the distal end 106 of the curing light 100, which is nearest the patient's teeth, mouth, and other sensitive tissue, may result in a more comfortable operation.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A dental curing light comprising:
an elongated housing having a proximal end and a distal end;
at least one light source disposed at the distal end of the housing, the light source and distal end being configured so as to be easily inserted into a patient's mouth when using the curing light to cure a dental composition;
an elongated heat sink, disposed within said housing, said elongated heat sink comprising a first portion adjacent to said light source and a second portion separated from the light source, and wherein the elongated heat sink is further comprised of:
a first layer comprising a first material having a first specific heat and a first thermal conductivity;

a second layer comprising a second material different from said first material, said second material having a second specific heat and a second thermal conductivity;

wherein the first layer surrounds the second layer so that the second layer forms a core within the first layer of the elongated heat sink, with the first layer contacting the light source; and wherein said first thermal conductivity is greater than said second thermal conductivity, and said second specific heat is greater than said first specific heat.

2. A dental curing light as recited in claim 1, wherein said first material comprises at least one of copper, aluminum, brass, steel, silver, another metal, a metal oxide ceramic, diamond, graphite, carbon fiber, a polymer based epoxy, silicon carbide, or silicone.

3. A dental curing light as recited in claim 1, wherein said second material comprises at least one of water, copper, nickel, magnesium, silicon or beryllium.

4. A dental curing light as recited in claim 1, wherein the core formed by said second material comprises one of a solid, liquid, or gas core within said heat sink.

5. A dental curing light as recited in claim 1, wherein said second layer comprises a material that undergoes a phase change between room temperature and about 135° C.

6. A dental curing light as recited in claim 1, wherein said material that undergoes a phase change is selected from the group comprising waxes, water, salts, fatty acids, fatty esters, polyols, metals, metal allows, hydrocarbons that change phase above room temperature and below about 135° C., iodine and gallium.

7. A dental curing light as recited in claim 1, wherein said heat sink further comprises a third layer comprising a third material disposed between the first and second layers, said third material having a thermal conductivity that is higher than the thermal conductivity of the second region.

8. A dental curing light as recited in claim 1, wherein said second layer comprises about half the volume of said heat sink.

9. A dental curing light as recited in claim 1, wherein said at least one light source comprises at least one LED.

10. A dental curing light as recited in claim 1, said at least one light source being powered by an external power source.

11. A dental curing light as recited in claim 1, further comprising an integral battery pack for powering said at least one light source.

12. A dental curing light as recited in claim 1, wherein said first material of said first layer has a thermal conductivity of at least about 120 J/sec-m-K.

13. A dental curing light as recited in claim 1, wherein said first material of said first layer has a thermal conductivity of at least about 240 J/sec-m-K.

14. A dental curing light as recited in claim 1, wherein said first material of said first layer has a thermal conductivity of at least about 350 J/sec-m-K.

15. A dental curing light as recited in claim 1, wherein said second material of said second layer has a specific heat of at least about 380 J/kg-K.

16. A dental curing light as recited in claim 1, wherein said second material of said second layer has a specific heat of at least about 900 J/kg-K.

17. A dental curing light as recited in claim 1, wherein said second material of said second layer has a specific heat of at least about 1800 J/kg-K.

18. A dental curing light as recited in claim 1, wherein the product of the density and specific heat of said second material is at least about 3 J/cm$^3$-K.

19. A dental curing light as recited in claim 1, wherein the product of the density and specific heat of said second material is at least about 3.3 J/cm$^3$-K.

20. A dental curing light as recited in claim 1, wherein the product of the density and specific heat of said second material is at least about 3.8 J/cm$^3$-K.

21. A dental curing light, comprising:

a housing having a proximal end and a distal end;

at least one LED light source disposed at the distal end of the housing, the light source and distal end being configured so as to be easily inserted into a patient's mouth when using the curing light to cure a dental composition;

an elongated heat sink, disposed within said housing, said elongated heat sink comprising a first portion located at a distal end of the heat sink so as to be adjacent to said light source and a second portion that is located toward a proximal end of the heat sink so as to be separated from the light source, and wherein the elongated heat sink is further comprised of:

a first layer comprising a first material having a first specific heat and a first thermal conductivity, said first layer being being in thermal contact with to said at least one LED light source;

a second layer comprising a second material different from said first material, said second material having a second specific heat and a second thermal conductivity, said second layer being in thermal contact with said first layer; and a third layer comprising a third material having a third specific heat and a third thermal conductivity, said third layer being in thermal contact with said second layer; and wherein the second layer continuously surrounds the third layer so that the third layer forms a core within the second layer of the elongated heat sink, and the first layer being disposed in thermal contact along the entire length of the second layer and being disposed between the light source and the second layer; and wherein said first thermal conductivity is greater than said second thermal conductivity, said second thermal conductivity is greater than said third thermal conductivity, and said third specific heat is greater than said first specific heat.

22. A dental curing light as recited in claim 21, wherein said third specific heat is also greater than said second specific heat.

23. A dental curing light as recited in claim 21, wherein said core comprises water.

* * * * *

UNITED STATES PATENT AND TRADEMARK OFFICE
CERTIFICATE OF CORRECTION

PATENT NO. : 7,056,116 B2  
APPLICATION NO. : 10/973537  
DATED : June 6, 2006  
INVENTOR(S) : Scott et al.

Page 1 of 1

It is certified that error appears in the above-identified patent and that said Letters Patent is hereby corrected as shown below:

Column 9  
Line 21, after "or gas", delete "core within said heat sink"

Column 10  
Line 29, after "first layer", delete "being"

Signed and Sealed this

Tenth Day of April, 2007

JON W. DUDAS  
*Director of the United States Patent and Trademark Office*